United States Patent [19]

Bruns et al.

[11] Patent Number: 4,555,359

[45] Date of Patent: Nov. 26, 1985

[54] TRIMETHYLBICYCLO [4.3.0] NON-1-ENE DERIVATIVES

[75] Inventors: Klaus Bruns; Ursula Weber, both of Krefeld-Traar, Fed. Rep. of Germany

[73] Assignee: Henkel Kommanditgesellschaft auf Aktien, Düsseldorf-Holthausen, Fed. Rep. of Germany

[21] Appl. No.: 458,744

[22] Filed: Jan. 18, 1983

[30] Foreign Application Priority Data

Apr. 2, 1982 [DE] Fed. Rep. of Germany ....... 3212326

[51] Int. Cl.$^4$ .......................... A61K 7/46; C11B 9/00
[52] U.S. Cl. ................................................ 252/522 R
[58] Field of Search ..................... 252/522 R; 568/374

[56] References Cited

U.S. PATENT DOCUMENTS

| | | | |
|---|---|---|---|
| 3,681,464 | 8/1972 | Theimer | 252/522 R X |
| 4,162,266 | 7/1979 | Helmlinger et al. | 252/522 R X |
| 4,206,089 | 6/1980 | Willis et al. | 252/522 R |
| 4,302,363 | 11/1981 | Bruns et al. | 252/522 R |
| 4,304,944 | 12/1981 | Willis et al. | 568/374 |

OTHER PUBLICATIONS

Chemical Abstracts, 88, 74232r, (1978).

*Primary Examiner*—Helen M. S. Sneed
*Attorney, Agent, or Firm*—Hammond & Littell, Weissenberger & Dippert

[57] ABSTRACT

Trimethylbicyclo [4.3.0] non-1-ene derivatives are fragrant substances which are suitable for use alone and in perfume and odorant compositions. Methods of preparation and representative compositions are also disclosed.

17 Claims, No Drawings

TRIMETHYLBICYCLO [4.3.0] NON-1-ENE DERIVATIVES

BACKGROUND OF THE INVENTION

The use of fragrances as perfumes and odorants has existed for as long as can be remembered. These substances were early obtained from suitable animal and plant sources, and since the nineteenth century synthetic fragrances have been prepared by chemists.

The requirements for a desirable fragrance are subjective and change with the fashion. This gives rise to a constant demand for new fragrances which may stand alone or act as compliments to those already available.

The problem faced by the synthetic chemist is the lack of predictability of success in producing an acceptable fragrance since it has yet to be established that there is any predictable relationship between chemical structure and fragrance characteristics or nuances.

U.S. Pat. No. 4,302,363 describes an isomer mixture of 4(5)-acetyl-7,7,9(7,9,9)-Trimethyl bicyclo[4.3.0]non-1-ene which is a valuable fragrance which has a warm ambergris odor.

OBJECT OF THE INVENTION

It is an object of the invention to provide a number of fragrant mixtures of isomer compounds.

Another object of the invention is to provide new fragrance mixtures having their own distinctive odor nuances.

It is a further object of the invention to provide perfume and odorant compositions containing the fragrant isomer mixtures of the invention.

Another object of the invention is to provide a method for the preparation of fragrant mixtures of isomer compounds.

A further object of the invention is to provide a fragrant mixture of three isomers of trimethylbicyclo[4.3.0]non-1-ene wherein the methyl groups are positioned in the respective isomers in the 7,9,9 7,7,9 and 6,8,8,-positions and is identified as 7,9,9(7,7,9/6,8,8)-trimethylbicyclo[4.3.0]non-1-ene.

These and other objects of the invention will become more apparent as the description thereof proceeds.

DESCRIPTION OF THE INVENTION

Now additional trimethylbicyclo[4.3.0]non-1-ene perfumes have been found which, too, are valuable perfumes with interesting and surprisingly different fragrance nuances. The new compounds are produced according to synthesis processes of organic chemistry known in themselves. As starting material one uses 2,2,4(2,4,4)-tri-methylcyclopentanone (I), which is always presents as an isomer mixture and is not obtainable as unitary compounds. This isomer mixture is transformed by Grignard reaction to the isomer mixture 1-vinyl-1-hydroxy-2,4,4 (and 2,4,4)-trimethylcyclopentane (II). Dehydration with p-toluene sulfonic acid gives 1-vinyl-2,4,4 (and 2,4,4)-trimethylcyclopent-1-ene (III), which consists of 3 isomers in each instance. The latter is transformed by Diels-Alder reaction with suitable dienophile aldehydes or ketones (compounds IV to IX) into corresponding trimethylbicyclo[4,3,0]non-1-ene derivatives of the invention which contain odorgenic acyl or aldehyde groups.

Suitable dienophile aldehydes or ketones, as used for the production of the compound of the invention, are selected from the group of consisting of acrolein, crotonaldehyde, ethylacrolein, pentene-3-one(2), emthyl-1-propenyl ketone and ethylvinyl ketone.

The odor nuances of the new compounds range between woody, green, sweet or respectively thujone, tobacco, coumarin, galbanum, spruce, ambergris scents and are outstanding for unusual lasting power. They can be mixed with other fragrances in the widest variety of proportions to produce new fragrance compositions. Generally the proportion in a fragrance composition ranges from between about 1 to 50 percent by weight, based on the total composition. Such compositions can be used to perfume cosmetic preparations, such as creams, lotions, colognes, aerosols, and toilet soaps, as well as in extract perfumery. But they may also be used for odor improvement of technical products such as washing and detergent products, softeners and textile treatment agents. For perfuming the various products, the compositions are generally added to them in concentrations of from 0.05 to 2 percent by weight, based on the total product.

The above described reaction process for the production of the new compounds can be represented by means of formulas as follows:

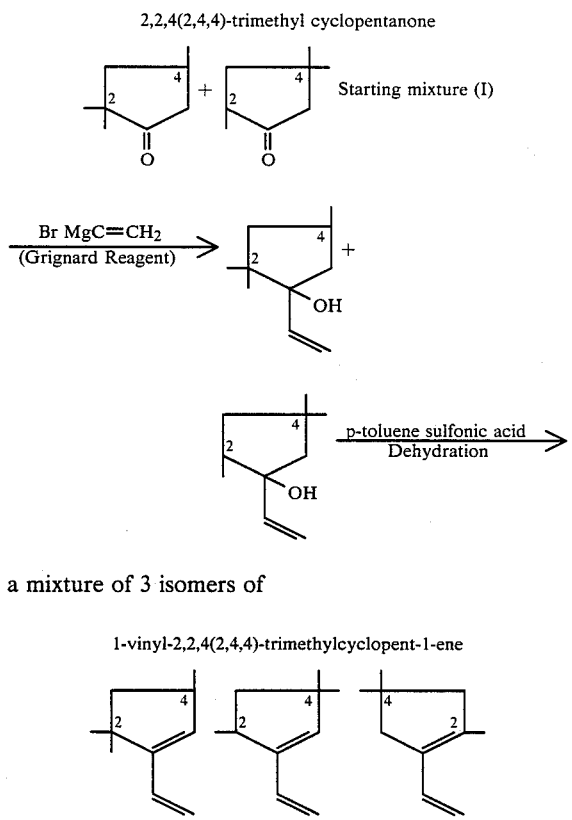

a mixture of 3 isomers of 1-vinyl-2,2,4(2,4,4)-trimethylcyclopent-1-ene

This mixture is subjected to Diels-Alder reaction with single (i.e., one reaction) dienophiles selected from the group consisting of:

| | |
|---|---|
| acrolein | (IV) |
| crotonaldehyde | (V) |
| ethylacrolein | (VI) |
| pentene-3-one(2) | (VII) |
| methyl isopropenyl ketone | (VIII) |
| ethyl vinyl ketone | (IX) |
| to form: | |

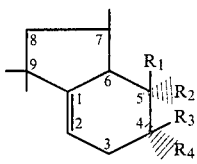

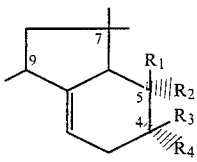

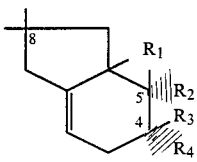

wherein depending on the dienophile used $R_1$, $R_2$, $R_3$ and $R_4$ have the following meanings:

When the dienophile is:

acrolein: when $R_1$ and $R_2$ are H, $R_3$ and $R_4$ are different, being either H or CHO; and when $R_3$ and $R_4$ are H then $R_1$ and $R_2$ are different being either CHO or H.

crotanaldehyde: when $R_1$ and $R_2$ are different, being either $CH_3$ or H, then $R_3$ and $R_4$ are different being either CHO or H; and when $R_3$ and $R_4$ are different being either $CH_3$ or H then $R_1$ and $R_2$ are different, being either CHO or H, ethylacrolein: when $R_1$ and $R_2$ are H, then $R_3$ and $R_4$ are different, being either CHO or $C_2H_5$; and when $R_3$ and $R_4$ are H, then $R_1$ and $R_2$ are different being either CHO or $C_2H_5$ pentene-3-one(2): when $R_1$ and $R_2$ are different, being either $CH_3$ or H, then $R_3$ and $R_4$ are different, being either $CH_3CO$ or H; and when $R_3$ and $R_4$ are different being either $CH_3$ or H, then $R_1$ and $R_2$ are different, being either $CH_3CO$ or H;

methyl isopropenyl ketone: when $R_1$ and $R_2$ are H, then $R_3$ and $R_4$ are different, being either $CH_3$ or $CH_3CO$; and when $R_3$ and $R_4$ are H, then $R_1$ and $R_2$ are different, being either $CH_3$ or $CH_3CO$ ethyl vinyl ketone: when $R_1$ and $R_2$ are H then $R_3$ and $R_4$ are different, being either $C_2H_5CO$ or H; and when $R_3$ and $R_4$ are H, then $R_1$ and $R_2$ are different, being $C_2H_5CO$ or H.

The new fragrances therefore are mixtures of 3 isomers in each instance, with acyl or respectively aldehyde groups and ring linkage ($C^6/C^7$) being able to occupy axial or equatorial configuration.

The following examples are given by way of illustration and not by way of limitation.

GENERAL PROCEDURE FOR THE DIELS-ALDER SYNTHESIS

Heat 0.1 mole of diene (III) with 0.1 to 0.12 mole of dienophile compounds IV to IX while stirring for 4 to 9 hours with reflux or in an autoclave at 200° C. (in the case of methyl-isopropenyl ketone (VIII) under nitrogen at 100° C.).

After completed reaction, distill unreacted diene or dienophile and fractionate the Diels-Alder adduct under oil pump vacuum.

EXAMPLE 1

Three isomers
7,9,9(7,7,9/6,8,8)-trimethylbicyclo[4.3.0]-non-1-ene-4e/a(5e/a)-carbaldehyde Reaction of (III) with acrolein in an autoclave, 4 hours at 200° C. B.p. 84°–88° C./0.6 mbar; GC: Isomer mixture.

IR (film): 2710, 1725/cm (CHO).

| $C_{13}H_{20}O$ | Calc. | Found |
|---|---|---|
| MG (GC/MS) | 192.3 | 192 (Isomer) |
| % C | 80.1 | 81.2 |
| % H | 10.5 | 10.4 |
| % O | 8.3 | 9.5 |

Odor: woody, thujone, camphor nuances

EXAMPLE 2

Three isomers
7,9,9(7,7,9/6,8,8)-trimethylbicyclo[4.3.0]-non-1-ene-4e/a(5e/a)-methyl,4e/a(5e/a)-carbaldehyde Reaction of (III) with crotonaldehyde in an autoclave, 6 hours at 200° C., B.p. 125°–135° C./18.6 mbar; isomer mixture.

IR (film): 2700, 1725/cm (CHO).

| $C_{14}H_{22}O$ | Calc. | Found |
|---|---|---|
| MG (GC/MS) | 206.3 | 206 (Isomer) |
| % C | 81.5 | 81.4 |
| % H | 10.75 | 10.90 |
| % O | 7.75 | 7.79 |

Odor: woody, straw nuances.

EXAMPLE 3

Three isomers
7,9,9,(7,7,9/6,8,8)-trimethylbicyclo[4.3.0]-non-1-ene-4e/a-ethyl,4a/e-carbaldehyde(5e/a-ethyl,5a/e-carbaldehyde Reaction of (III) with ethylacrolein in an autoclave, 6 hours at 200° C.

B.p. 105°–115° C./2 mbar: GC: isomer mixture.
IR (film): 2700, 1723/cm (CHO).

| $C_{15}H_{24}O$ | Calc. | Found |
|---|---|---|
| MG (GC/MS) | 220.4 | 220 (Isomer) |
| % C | 81.76 | 80.90 |
| % H | 10.98 | 10.60 |
| % O | 7.26 | 8.30 |

Odor: Tobacco, coumarin nuances

EXAMPLE 4

Three isomers
4a/e(5a/e)-acetyl-5a/e(4a/e-methyl,7,9,9(7,9,9/6,8,8)-trimethylbicyclo[4.3.0]non-1-ene Reaction of (III) with penten-3-one-(2) in an autoclave, 9 hours at 200° C.

B.p. 95°–105° C./2.4 mbar; GC: isomer mixture.
IR (film): 1710/cm (C=O); 1151/cm ($COCH_3$).

1350–1375/cm (mixed di-methyl, COCH$_3$).

| C$_{15}$H$_{24}$O | Calc. | Found |
|---|---|---|
| MG (GC/MS) | 220.4 | 220 (Isomer) |
| % C | 81.76 | 81.25 |
| % H | 10.98 | 10.80 |
| % O | 7.26 | 8.42 |

Odor: woody, sweet, ambergris, warm spruce, allylionone nuances.

EXAMPLE 5

Three isomers
4e/a(5e/a)-acetyl-4a/e(5a/e)-methyl,7,9,9(7,7,9/6,8,8)-trimethylbicyclo[4.3.0]non-1-ene Reaction of (III) with methylisopropenyl ketone at 100° C., 4 hours reflux (N$_2$ atmosphere).
B.p. 81°–87° C./0.3 mbar; GC: isomer mixture.
IR (film): 1708/cm (C=O); 1153/cm (COCH$_3$); 1350–1380 (mixed di-methyl, COCH$_3$); 3030, 810/cm (>C=CH).

| C$_{15}$H$_{24}$O | Calc. | Found |
|---|---|---|
| MG (GC/MS) | 220.4 | 220 (Isomer) |
| % C | 81.76 | 81.80 |
| % H | 10.98 | 11.00 |
| % O | 7.26 | 7.30 |

Odor: Galbanum, dipentene nuances.

EXAMPLE 6

4e/a(5e/a)-Propionyl-7,9,9(7,7,9/6,8,8)-trimethylbicyclo[4.3.0]non-1-ene

Reaction of (III) with ethylvinyl ketone at 170° C., 2 hours reflux.
B.p. 105°–115° C./4 mbar: GC: isomer mixture.
IR (film): 1710/cm (C=O); 3020, 1340, 805 (>C=CH).

| C$_{15}$H$_{24}$O | Calc. | Found |
|---|---|---|
| MG (GC/MS) | 220.4 | 220 (Isomer) |
| % C | 81.76 | 80.80 |
| % H | 10.98 | 11.30 |
| % O | 7.26 | 8.35 |

Odor: green, green bean pod nuances

EXAMPLE 7

Examples of composition

| (a) Wood base: | |
|---|---|
| 4e/a(5e/a-acetyl-4e/a(5a/e)-methyl, 7,7,9(7,9,9/6,8,8)-trimethylbicyclo[4.3.0]non-1-ene | 300 parts by weight |
| vetiverylacetate (Vetiveryl acetate) | 250 " |
| Sandela ® (Givaudan) | 150 " |
| Patchouliol (Patchouli oil) | 50 " |
| Ketonmoschus (Ketone musk) | 30 " |
| Eichenmoos Absolute (Oakmoss Absolute) | 20 " |
| Labdanum Resin | 10 " |
| Myrrhe Resin (Myrrh resin) | 5 " |
| Pfefferol (Pepper oil) | 5 " |
| Muskatnusol (Nutmeg oil) | 5 " |
| Cistusol (Cistus oil) | 5 " |
| Eugenol | 5 " |

| | 1000 parts by weight |
|---|---|
| (b) Fern-like perfume | |
| 7,9,9(7,7,9/6,8,8)-trimethylbicyclo[4.3.0]-non-1-ene-4e/a-ethyl, 4a/e-carbaldehyde (5e/a-ethyl,5a/3-carbaldehyde) | 50 parts by weight |
| Formaldehyde-cyclododecyl ethyl acetal | 150 " |
| Bergamot oil | 150 " |
| Methyl cyclo-octyl carbonate | 100 " |
| Methyl ionone | 80 " |
| Lavandin oil | 80 " |
| Citronellol | 50 " |
| Citral | 40 " |
| Musk ambrette | 40 " |
| Oakmoss Absolute | 40 " |
| Rosemary oil | 30 " |
| Orange oil | 30 " |
| Ilang-ilang oil | 30 " |
| Vetiver oil | 20 " |
| Lavandin Absolute | 20 " |
| Benzyl isoeugenol | 15 " |
| Cinnamon leaf oil | 15 " |
| Coriander oil | 15 " |
| Labdanum absolute | 15 " |
| Eugenol | 10 " |
| Patchouli oil | 10 " |
| Thyme oil | 10 " |
| | 1000 parts by weight |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A fragrant mixture of three isomers of trimethylbicyclo[4.3.0]non-1-ene wherein the methyl groups are positioned in the respective isomers in the 7,9,9, the 7,7,9 and the 6,8,8 positions and which are substituted in the 4 and 5 positions by substituents selected from the group consisting of hydrogen, lower alkyl, carbaldehyde and lower alkanoyl wherein at least one carbaldehyde or one lower alkanoyl is present in either the 4 or 5 position but not in both.

2. A fragrant mixture of isomers as set forth in claim 1 which is 7,9,9(7,7,9/6,8,8)-trimethylbicyclo[4.3.0]non-1-ene-4e/a(5e/a)-carbaldehyde.

3. A fragrant mixture of isomers as set forth in claim 2 which is 7,9,9(7,7,9/6,8,8)-trimethylbicyclo[4.3.0]non-1-ene-4e/a(5e/a)-methyl,4e/a(5e/a)-carbaldehyde.

4. The fragrant mixture of isomers set forth in claim 1 which is 7,9,9(7,7,9/6,8,8)-trimethylbicyclo[4.3.0]non-1-ene-4e/a-ethyl,4a/e-carbaldehyde(5e/a-ethyl,5a/e-carbaldehyde).

5. The fragrant mixture of isomers set forth in claim 1 which are 7,9,9(7,7,9/6,8,8)-trimethylbicyclo[4.3.0]non-1-ene-4e/a(5e/a)-acetyl-4a/e(5a/e)-methyl.

6. The fragrant mixture of isomers are set forth in claim 1 which is 7,9,9(7,7,9/6,8,8)-trimethylbicyclo[4.3.0]non-1-ene-4e/a(5e/a)-acetyl-4a/e(5a/e)-methyl.

7. The fragrant mixture of isomers set forth in claim 1 which is 7,9,9(7,7,9/6,8,8)-trimethylbicyclo[4.3.0]non-1-ene-4e/a)5e/a)-propionyl.

8. A method for the production of 7,9,9(7,7,9/6,8,8)trimethylbicyclo[4.3.0]non-1-ene derivatives by reacting 2,2,4(2,4,4)-trimethylcyclopentanone in a Grignard reaction using vinyl magnesium bromide to obtain 1-vinyl-1-hydroxy-2,2,4(2,4,4)-trimethylcyclopentane, dehydrating this product to obtain 1-vinyl-2,2,4(2,4,4)-trimethylcyclo-pent-1-ene, reacting the second product with a dienophile aldehyde or ketone, selected from the group consisting of acrolein, crotonaldehyde, ethylacrolein, pentene-3-one (2), methylisopropenyl ketone and ethyl-vinyl ketone to obtain 7,9,9(7,7,9/6,8,8)-trimethylbicyclo[4.3.0]non-1-ene derivatives.

9. A fragrance composition consisting essentially of 7,9,9(7,7,9/6,8,8)-trimethylbicyclo[4.3.0]non-1-ene derivatives.

10. A fragrance composition as set forth in claim 9 wherein 7,9,9(7,7,9/6,8,8)-trimethylbicyclo[4.3.0]non-1-ene derivatives is combined with other fragrances and materials found in such compositions in an amount of from about 1 to 50% by weight based on the total composition.

11. A fragrance composition as set forth in claim 9 in combination with various commercial products in amounts of from about 0.05 to 2.0% by weight based on the total finished product.

12. A mixture of isomers comprising 7,9,9(7,7,9/6,8,8)-trimethylbicyclo[4.3.0]non-1-ene; 7,9,9(7,7,9/6,8,8)-trimethylbicyclo[4.3.0]non-1-ene, 4e/a(5e/a)-carbaldehyde, 7,9,9(7,7,9/6,8,8)-trimethylbicyclo[4.3.0]non-1-ene-4e/a(5e/a)-methyl,4e/a(5e/a)-carbaldehyde; 7,9,9(7,7,9/-6,8,8)-trimethylbicyclo[4.3.0]non-1-ene-4e/a-ethyl, 4a/e-carbaldehyde(-5e/a-ethyl,5a/e-carbaldehyde); 7,7,9(7,9,9/6,8,8)-trimethylbicyclo[4.3.0]non-1-ene-4e/a(5e/a)-acetyl-4a/e(-5a/e)-methyl, 7,9,9(7,7,9/6,8,8)-trimethylbicyclo[4.3.0]-non-1-ene-4e/a(5e/a)-acetyl-4a/e(5a/e)-methyl; y or 7,9,9(7,7,9/6,8,8)-trimethylbicylo[4.3.0]non-1-ene-4e/a(5e/a)-propionyl.

13. A perfume composition comprising an effective amount of a mixture of the isomers of claim 12.

14. The perfume composition of claim 13, which comprises from about 1 to 50 percent by weight of said isomer mixture, the remainder comprising customary constituents of perfume compositions.

15. The perfume composition of claim 14, wherein said customary constituents of perfume compositions include at least one other perfume.

16. The method of imparting a desired aroma to a product which comprises administering an aroma-imparting amount of the perfume composition of claim 13.

17. The method of claim 16, wherein from about 0.05 to 2 percent by weight of the perfume composition is administered.

* * * * *

UNITED STATES PATENT AND TRADEMARK OFFICE
CERTIFICATE OF CORRECTION

PATENT NO. : 4,555,359                                        Page 1 of 2
DATED      : November 26, 1985
INVENTOR(S) : KLAUS BRUNS et al.

It is certified that error appears in the above-identified patent and that said Letters Patent is hereby corrected as shown below:

Column 3, line 33, "crotanaldehyde" should read -- crotonaldehyde --;

line 36, "H" should read -- H, --;

line 40, "different" should read -- different, --;

line 44, "different" should read -- different, --;

line 51, "H" should read -- H, -- .

Column 4, line 63, the moiety "4a/e(5a/e)-acetyl-5a/e(4a/e" should read -- 4e/a(5e/a)-acetyl-4a/e(5a/e) --.

Column 5, line 36, "ethylvinyl" should read -- ethyl vinyl --;

line 56, the moiety "4e/a(5e/a" should read -- 4e/a(5e/a) --.

UNITED STATES PATENT AND TRADEMARK OFFICE
CERTIFICATE OF CORRECTION

PATENT NO. : 4,555,359

Page 2 of 2

DATED : November 26, 1985

INVENTOR(S) : KLAUS BRUNS et al.

It is certified that error appears in the above-identified patent and that said Letters Patent is hereby corrected as shown below:

Column 6, Claim 7, line 3, the moiety "4e/a)5e/a) should read
-- 4e/a(5e/a) --.

Column 8, line 5, the moiety "5a/e)-methyl," should read
-- 5a/e)-methyl; --;

Column 8, line 6, "y or" should read -- or --.

Signed and Sealed this

Twenty-fifth Day of March 1986

[SEAL]

*Attest:*

DONALD J. QUIGG

*Attesting Officer*  *Commissioner of Patents and Trademarks*